United States Patent
Yan et al.

(10) Patent No.: US 10,207,980 B2
(45) Date of Patent: *Feb. 19, 2019

(54) PROCESS FOR FORMING AMINE BY DIRECT AMINATION REACTION

(71) Applicants: RHODIA OPERATIONS, Paris (FR); CENTRE NATIONAL DE LA RECHERCHE SCIENTIFIQUE, Paris (FR)

(72) Inventors: Zhen Yan, Shanxi (CN); Marc Pera Titus, Shanghai (CN); Armin T. Liebens, Shanghai (CN)

(73) Assignee: RHODIA OPERATIONS, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/525,632

(22) PCT Filed: Nov. 10, 2014

(86) PCT No.: PCT/CN2014/090695
§ 371 (c)(1),
(2) Date: May 10, 2017

(87) PCT Pub. No.: WO2016/074121
PCT Pub. Date: May 19, 2016

(65) Prior Publication Data
US 2017/0320811 A1    Nov. 9, 2017

(51) Int. Cl.
C07C 209/16 (2006.01)
B01J 23/44 (2006.01)
B01J 23/63 (2006.01)

(52) U.S. Cl.
CPC ............ *C07C 209/16* (2013.01); *B01J 23/44* (2013.01); *B01J 23/63* (2013.01)

(58) Field of Classification Search
None
See application file for complete search history.

(56) References Cited

U.S. PATENT DOCUMENTS

| | | | |
|---|---|---|---|
| 4,209,424 A | 6/1980 | Le Goff et al. | |
| 4,942,261 A | 7/1990 | Ishimura et al. | |
| 7,514,585 B2 | 4/2009 | Fukushima et al. | |
| 8,318,982 B2 | 11/2012 | Kubanek et al. | |
| 9,663,446 B2 | 5/2017 | Yan et al. | |

FOREIGN PATENT DOCUMENTS

| | | |
|---|---|---|
| CN | 102203108 A | 9/2011 |
| CN | 102503836 A | 6/2012 |
| CN | 103097324 A | 5/2013 |
| CN | 103228612 A | 7/2013 |
| CN | 103599776 A | 2/2014 |
| EP | 300852 B1 | 9/1991 |
| EP | 388567 B1 | 3/1995 |
| KR | 20120003212 A | 1/2012 |
| WO | 2014094650 A1 | 6/2014 |
| WO | 2015054828 A1 | 4/2015 |
| WO | 2016074121 A1 | 5/2016 |

OTHER PUBLICATIONS

Bahn et al., "The Catalytic Amination of Alcohols", ChemCatChem 2011, vol. 3, pp. 1853-1864.
Guillena et al., "Hydrogen Autotransfer in the N-Alkylation of Amines and Related Compounds using Alcohols and Amines as Electrophiles", Chemical Reviews 2010, vol. 110, pp. 1611-1641.
Nixon et al., "Transition metal catalysed reactions of alcohols using borrowing hydrogen methodology", Dalton Translations, 2009, pp. 753-762.
Cano et al., "Impregnated Ruthenium on Magnetite as a Recyclable Catalyst for the N-Alkylation of Amines, Sulfonamides, Sulfinamides, and Nitroarenes Using Alcohols as Electrophiles by a Hydrogen Autotransfer Process," The Journal of Organic Chemistry, 2011, vol. 76, pp. 5547-5557.
Corma et al., "A Bifunctional Pd/MgO Solid Catalyst for the One-Pot Selective N-Monoalkylation of Amines with Alcohols", Chemistry, A European Journal 2010, vol. 16, pp. 254-260.
Zhang et al., "Palladium catalyzed N-alkylation of amines with alcohols", Tetrahedron Letters 52, 2011, pp. 1334-1338.
Brunauer et al., "Adsorption of Gases in Multimolecular Layers", The Journal of American Society, vol. 60, pp. 309-319, Feb. 1983.
Y.-F. Han et al., "Kinetics of ethylene combustion in the synthesis of vinyl acetate over a Pd/SiO2 catalyst", Journal of Catalysis, vol. 224, 2004, pp. 60-68.
Corma et al., "Coupling of Two Multistep Catalytic Cycles for the One-Pot Synthesis of Propargylamines from Alcohols and Primary Amines on a Nanoparticulated Gold Catalyst", Chemistry, A European Journal 2012, vol. 18, pp. 14150-14156.
Shimizu et al., "Heterogeneous Ni Catalyst for Direct Synthesis of Primary Amines from Alcohols and Ammonia", ACS Catalysis, 2013, vol. 3, pp. 112-117.
Jalal Albadi et al., "Green Recyclable CuO—CeO2 Nanocomposite Catalyzed Amination of Aryl Halides with Aqueous Ammonia in Water", Chinese Journal of Chemistry, 2014, vol. 32, pp. 396-398.

*Primary Examiner* — Jafar F Parsa
*Assistant Examiner* — Jennifer C Sawyer

(57) ABSTRACT

Providing a process for forming an amine, such as a primary, a secondary or a tertiary amine, via the direct amination of an alcohol using a catalyst comprising at least a palladium compound on a support comprising cerium oxide.

14 Claims, No Drawings

PROCESS FOR FORMING AMINE BY DIRECT AMINATION REACTION

This application is a U.S. national phase entry under 35 U.S.C. § 371 of International Application No. PCT/CN2014/090695, filed on Nov. 10, 2014, the entirety of which is explicitly incorporated herein by this reference.

The present invention concerns a process for forming an amine, such as a primary, a secondary or a tertiary amine, via the direct amination of an alcohol of by using a catalyst comprising at least a palladium compound on a support comprising a cerium oxide.

PRIOR ART

The following discussion of the prior art is provided to place the invention in an appropriate technical context and enable the advantages of it to be more fully understood. It should be appreciated, however, that any discussion of the prior art throughout the specification should not be considered as an express or implied admission that such prior art is widely known or forms part of common general knowledge in the field.

Amines are of significant importance to the chemical industry. These synthetic amines are used as solvents, agrochemicals, pharmaceuticals, detergents, fabric softeners, flotation agents, corrosion inhibitors, antistatic additives, lubricants, polymers, varnishes, and dyes. A variety of procedures have been developed for the synthesis of organic amines, such as hydroamination, reduction of nitriles and nitro compounds, or reductive amination (S. Bähn, S. Imm, L. Neubert, M. Zhang, H. Neumann, M. Beller, ChemCatChem 3 (2011) 1853). The feedstocks for many of these processes are ketones, aldehydes, nitriles, carboxylic acids, alkyl halides or alkenes.

With the development of many biomass-based processes and technologies, alcohols become a potential and promising source for the chemical industrial, including the synthesis of amines.

Direct amination of alcohols is a very attractive pathway to prepare amines because water is the only byproduct for this process. Various techniques have been described in the literature but usually require stringent conditions such as high temperature or high pressure of hydrogen.

The reaction between alcohol and ammonia is the most common method for the manufacture of lower alkyl amines. Dehydrogenation catalysts based on nickel, cobalt, iron and copper are used and the reaction typically takes place at 0.5-20 MPa at temperatures of 100-250° C. Hydrogen is added to the mixture to maintain the activity of the metal surface of the catalyst.

Generally, aldehydes and ketones are used in preference to alcohols as raw materials for amine synthesis. The reductive amination reaction is usually described to proceed in two stages, as shown below:

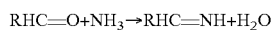

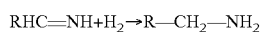

Hydrogenation of nitriles is also used to produce some amines. Hydrogen is consumed stoichiometrically in such types of processes.

Amines are also prepared by the reaction of olefins with hydrocyanic acid followed by reduction or the reaction of alkyl halides with ammonia. These processes usually involve hazardous reagents such as HCN, or generate hazardous byproducts such as HCl. The neutralization of HCl using a base generates 2 eq. NaCl per 1 eq. of diamine generated, making the process environmentally unfriendly.

As a shift from fossil feedstock, it appears that the use of biomass as a feedstock will lead to the production of many different alcohols. Therefore, direct amination of alcohols with ammonia or amines with water as the only byproduct becomes a very important pathway for the synthesis of amines:

$$R^1\text{—OH} + R^2R^3\text{NH} \rightarrow R^1R^2R^3\text{—N} + H_2O$$

($R^1$=alkyl/$R^2$, $R^3$=H or alkyl)

There have been significant amount of studies in the literature on the direct amination of alcohols, such as G. Guillena, D. J. Ramón, M. Yus, Chem. Ver. 110 (2009) 1611 and T. D. Nixon, M. K. Whittlesey, J. M. J. Williams, Dalton Trans 0 (2009) 753. The most studied systems for the synthesis of amines from alcohols are based on homogeneous organometallic catalysts. Ru and Ir-based complexes are the most widely used and have been shown to have good to excellent yields for the amination of a variety of alcohols. So far, no homogeneously catalyzed alcohol amination has been employed on industrial scale as mentioned in S. Bähn, S. Imm, L. Neubert, M. Zhang, H. Neumann, M. Beller, ChemCatChem 3 (2011) 1853.

Heterogeneously catalyzed amination of alcohols has also been reported, although less common compared to its homogeneous counterpart. The group of Mizuno investigated heterogeneous ruthenium catalysts for the N-alkylation of primary and secondary amines with primary alcohols. Applying the supported ruthenium hydroxide catalyst Ru(OH)x/Al$_2$O$_3$, anilines were selectively N-monoalkylated to give the following secondary amine products:

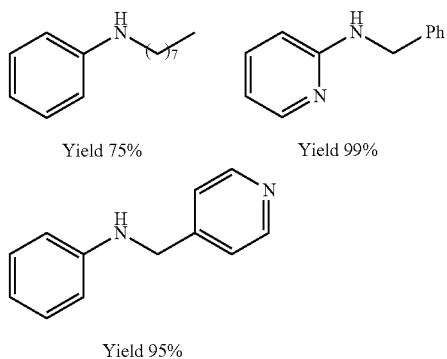

Cano and co-workers reported impregnated ruthenium on magnetite to catalyze the N-alkylation of aromatic amines with primary benzylic alcohols to give secondary amines (R. Cano, D. J. Ramón, M. Yus, J. Org. Chem. 76 (2011) 5547).

Pd catalysts supported on certain oxides also show promising performance for the N-alkylation of amines with alcohols. Corma et al. reported that a Pd/MgO catalyst is highly selective for the monoalkylation of aniline with benzyl alcohol (A. Corma, T. Ródenas, M. J. Sabater, Chem.-Eur. J. 16 (2010) 254). Shi et al. showed that an iron oxide-supported Pd catalysts exhibits high yields for reactions of amines and alcohols with various structures (Y. Zhang, X. Qi, X. Cui, F. Shi, Y. Deng, Tetrahedron Lett. 52 (2011) 1334).

INVENTION

It appears now that it is perfectly possible to produce at least one amine, such as a primary, a secondary or a tertiary amine, by direct amination of an alcohol by using a catalyst comprising at least a palladium compound on a support comprising cerium oxide; said catalyst showing much higher activity and selectivity than conventional amination catalysts, including Pd catalysts supported on other materials, such as alumina, silica, activated carbon, and titania. It also appears that this catalyst is stable during the direct amination reaction of the invention and both the activity and selectivity of said catalyst are the same with fresh catalyst or yet used catalyst.

The present invention concerns then a process to produce at least one amine, notably a primary, a secondary or a tertiary amine, comprising at least reacting of:
1) a first reactant being an alkyl alcohol comprising one primary or secondary hydroxyl group; and
2) a second reactant being ammonia and/or an ammonia source;
in the presence of a catalyst comprising at least a palladium compound on a support comprising a cerium oxide.

Preferably, the present invention concerns a process to produce at least one amine, preferably a primary, a secondary or a tertiary amine, comprising at least reacting of:
1) a first reactant being a compound of formula (I) $R^1$—OH or formula (II) $R^2$—C(OH)—$R^3$, wherein $R^1$, $R^2$, and $R^3$ are independently an alkyl group comprising from 1 to 40 carbon atoms; and
2) a second reactant being ammonia and/or an ammonia source;
in the presence of a catalyst comprising at least a palladium compound on a support comprising a cerium oxide.

The invention also concerns an amine, notably a primary, a secondary or a tertiary amine, obtained by the above identified process.

Other characteristics, details and advantages of the invention will emerge even more fully upon reading the description which follows.

Definitions

Throughout the description, including the claims, the term "comprising one" should be understood as being synonymous with the term "comprising at least one", unless otherwise specified, and "between" should be understood as being inclusive of the limits.

As used herein, "alkyl" groups include saturated hydrocarbons having one or more carbon atoms, including straight-chain alkyl groups, such as methyl, ethyl, propyl, butyl, pentyl, hexyl, heptyl, octyl, nonyl, decyl, cyclic alkyl groups (or "cycloalkyl" or "alicyclic" or "carbocyclic" groups), such as cyclopropyl, cyclopentyl, cyclohexyl, cycloheptyl, and cyclooctyl, branched-chain alkyl groups, such as isopropyl, tert-butyl, sec-butyl, and isobutyl, and alkyl-substituted alkyl groups, such as alkyl-substituted cycloalkyl groups and cycloalkyl-substituted alkyl groups. In complex structures, the chains may be branched, bridged, or cross-linked.

As used herein, "alkyl alcohol" refers to an aliphatic alcohol in which the aliphatic alkane chain is substituted by a hydroxyl group at unspecified position.

DETAILS OF THE INVENTION

Catalyst of the present invention comprises at least a palladium compound on a support comprising a cerium oxide. Preferably the support comprises between 50-100% by weight of cerium oxide, more preferably between 70-100% by weight of cerium oxide, bases on the total weight of the support. More preferably, the support consist essentially of cerium oxide, notably the support is consisting of cerium oxide.

It is well known in the art that cerium oxide may be used as a catalyst or a catalyst support. Several cerium oxides may be used for this purpose.

Cerium oxide of the present invention may provide a specific surface comprised between 50 and 300 $m^2/g$, notably between 200 and 280 $m^2/g$, measured after calcination at a temperature of 350° C. for 2 hours. "Specific surface" notably means the specific B.E.T. surface determined by nitrogen adsorption in accordance with the ASTM D 3663-78 standard established by the BRUNAUER-EMMETT-TELLER method described in "The Journal of American Society, 60, 309 (1938)".

Cerium oxide of the present invention may provide a specific surface of at least 200 $m^2/g$, preferably between 200 and 400 $m^2/g$, measured after calcination at a temperature of 400° C. for 2 hours.

Cerium oxide of the present invention may provide a specific surface of at least 15 $m^2/g$, notably between 20 and 60 $m^2/g$, measured after calcination at a temperature of 800° C. for 2 hours.

Cerium oxide of the present invention may provide a porous volume of greater than 0.1 $cm^3/g$, preferably greater than 0.15 $cm^3/g$, notably between 0.15 and 0.25 $cm^3/g$, at a measurement temperature of 800° C. for 2 hours. The porous volume, which corresponds to pores with a diameter of less than 60 nm, is measured with a mercury porosimeter in accordance with the ASTM D4284-83 standard or using the isotherm nitrogen adsorption method (the above-identified B.E.T. method).

These cerium oxides are notably described in the EP300852 and EP388567 publications.

These cerium oxide supports may be obtained by calcination of a ceric hydroxide in which the cerium hydroxide is subjected to solvothermal treatment before calcination.

These cerium oxide supports may notably be obtained according to the following process consisting of:
preparing a ceric hydroxide by reacting a solution of cerium salt and a base, possibly in the presence of an oxidizing agent, with the amount of the base being such that the pH of the reaction medium is greater than 7; of separating the precipitate obtained, and possibly washing it;
placing the ceric hydroxide in suspension in water or in an aqueous solution of a decomposable base;
heating it in a closed chamber to a temperature and a pressure respectively lower than the critical temperature and the critical pressure of said medium;
cooling the reaction mixture and bringing it to atmospheric pressure;
separating the ceric hydroxide treated in this manner; then calcining it.

Cerium oxide particles may also comprise at least one rare earth element oxide, other than cerium oxide, an alkaline earth metal oxide, a transition metal element oxide, a post-transition metal element oxide, or a metalloid element oxide, notably in a proportion comprised between 1 and 40% by weight of oxide, preferably in a proportion comprised between 1 and 20% by weight of oxide.

Rare earth element (REE) or rare earth metal is one of a set of seventeen chemical elements in the periodic table, meaning the fifteen lanthanides plus scandium and yttrium. Preferably, the rare earth element oxide are chosen in the group consisting of: lanthanium oxide ($La_2O_3$), praseodymium oxide ($Pr_6O_{11}$), neodymium oxide ($Nd_2O_3$) and yttrium oxide ($Y_2O_3$).

Transition metal element oxide may be for instance $ZrO_2$ and $TiO_2$. Post-transition metal element oxide may be for instance $Al_2O_3$, CuO and ZnO. Metalloid element oxide may be for instance $SiO_2$. Alkaline earth metal oxide may be for instance BaO.

Preferred mixed oxides of the present invention are chosen in the group consisting of: $CeO_2$—$ZrO_2$, $CeO_2$—$SiO_2$, $CeO_2$—$Pr_2O_3$, and $CeO_2$—$ZrO_2$—$La_2O_3$.

Palladium compound of the present invention may be palladium metal itself or any compound comprising palladium such as for example salts or oxides of palladium.

Palladium compounds are preferably chosen in the group consisting of: palladium metal, PdO, $PdO_2$, palladium nitrate, palladium chloride, palladium acetate, palladium acetylacetonate, and palladium hydroxide.

Catalysts composed of a cerium oxide support and comprising at least a palladium compound may be obtained by several know methods such as for example impregnation or co-precipitation, notably incipient wetness impregnation. Several palladium compounds or palladium compound precursors may be used such as for example palladium(II) nitrate dehydrate, palladium chloride, palladium acetate, palladium acetylacetonate, and palladium hydroxide.

Impregnation of an appropriate catalyst support is notably mentioned in Y.-F. Han et al. Journal of Catalysis 224 (2004) 60.

The activation or re-activation of the catalysts may involve a calcination step and/or a reduction step under hydrogen. Notably, the activation of the modified catalysts may involve a calcination step under air or $O_2$ at 100-500° C. for 1-24 hours and a reduction step under hydrogen at the same temperature for 1-6 hours. It is also possible to activate the catalyst of the present invention by reduction in a flow of hydrogen at 100-500° C.

The concentration of palladium compound on cerium oxide may be comprised between 0.1 and 20% by weight, preferably from 0.5 to 10% by weight.

The weight ratio of the catalyst of the present invention to the second reactant may be comprised between 0.05 and 2, preferably from 0.1 to 0.5.

First reactant used in the process of the present invention is then an alkyl alcohol comprising one primary or secondary hydroxyl group. Alkyl chain of the alkyl alcohol may comprise from 1 to 40 carbon atoms, preferably from 4 to 20 carbon atoms, more preferably from 6 to 12 carbon atoms.

First reactant used in the process of the present invention may be a primary alcohol of formula (I) $R^1$—OH or a secondary alcohol of formula (II) $R^2$—C(OH)—$R^3$, wherein $R^1$, $R^2$, and $R^3$ are independently an alkyl group comprising from 1 to 40 carbon atoms, preferably from 4 to 20 carbon atoms, more preferably from 6 to 12 carbon atoms.

The alkyl group of the first reactant may be straight or branched, and may optionally comprise one or several heteroatoms such as O, S, F, and N.

Preferred first reactants of the present invention, such as compounds of formula (I), are chosen in the group consisting of: 1-butanol, 1-hexanol, 1-octanol, 1-decanol and 1-dodecanol. Preferred first reactants of the present invention, such as compounds of formula (II), are chosen in the group consisting of: 2-butanol, 2-hexanol, 3-hexanol, 2-octanol, 3-octanol and 4-octanol.

It has to be noticed that it's perfectly possible to use several first reactant types during the reaction of the present invention.

Concentration of the first reactant may be comprised between 0.001 and 10 mol·$L^{-1}$, when a solvent is used in the reaction medium.

Second reactant of the invention is ammonia and/or an ammonia source that is a compound able to generate ammonia ($NH_3$) in the conditions of the reaction. Ammonia in the reaction may be for instance gaseous ammonia, liquid ammonia, or an ammonia solution in solvent, such as water. Ammonia source may be for instance an ammonium salts, such as ammonium carbonate and ammonium bicarbonate.

Concentration of the second reactant may be comprised between 0.001 and 10 mol·$L^{-1}$, when a solvent is used in the reaction medium.

The amine obtained according to the process of the present invention may be a primary, a secondary or a tertiary amine, preferably a primary or a secondary amine.

The primary or secondary amine of the present invention may notably be a compound of formula (III), (IV) or (V):

$$R^1\text{—}NH_2 \qquad (III)$$

$$(R^1)_2\text{—}NH \qquad (IV)$$

$$(R^1)_3\text{—}N \qquad (V)$$

Preferred primary or second amines of the invention, such as compounds of formula (III), (IV) or (V), are chosen in the group consisting of: octylamine, dioctylamine, trioctylamine, butylamine, dibutylamine, tributylamine, hexylamine, dihexylamine, trihexylamine, decylamine, didecylamine, tridecylamine, dodecylamine, didodecylamine, and tridodecylamine.

Process of the present invention is carried out at a temperature and for a time sufficient for an amine, preferably primary, secondary or tertiary amine, to be produced.

According to a particular embodiment of the present invention, the reaction medium can comprise, notably at the start of the reaction, between 0.1 and 50 molar equivalent of the second reactant for 1 molar equivalent of the first reactant, notably between 0.1 and 5 molar equivalent of the second reactant for 1 molar equivalent of the first reactant, notably between 0.1 and 1 molar equivalent of the second reactant for 1 molar equivalent of the first reactant in order to selectively produce secondary amine products in the reaction.

The process of the present invention may be carried out without solvent.

It is also possible to use a solvent or a combination of solvents for the reaction, notably solvents able to dissolve the first reactant and the second reactant. Preferred solvents to be used in the process of the invention are polar protic solvents, notably alcohols such as tert-amyl alcohol, isopropanol, ethanol, propanol and methanol, A nonlimiting selection of suitable organic solvents encompasses benzene, toluene, the xylene isomers, mesitylene, dioxane, THF, dimethoxyethane, anisole and cyclohexane.

A combination of two or more solvents in blend may be used during the reaction of the present invention.

The temperature at which reaction is performed may vary in a large range, but in general it is preferred that the reaction is carried out at a temperature from 100 and 250° C., more preferably between 150 and 200° C. Temperatures may be reached either thermally or by microwave irradiation.

Pressure range of the reaction may be comprised between 1 and 100 bar. Reaction of the present invention may be carried out for a range time comprised between 10 min to 24 hours, preferably between 1 hour and 8 hours.

The reaction may be carried out in the presence of air, hydrogen, or an inert atmosphere such as $N_2$, Ar, and $CO_2$. An inert or hydrogen atmosphere is preferred.

This reaction may be conducted in any conventional equipment suitable to effect production of amines. This reaction may be carried out in a continuous or a discontinuous fashion. For example, suitable equipment include a stirred tank or loop reactor.

The reaction may be carried out with one or both reactants in their gas phase. Suitable equipments include a fixed-bed reactor or a fluidized bed reactor. End of reaction may be carried out by stop of the temperature and cooling of the reaction medium, notably air cooling.

The efficiency of the process of the present invention can be monitored by any conventional analytical means, such as Infrared spectroscopy, NMR, Raman spectroscopy, GC, HPLC and SFC.

At the end of the reaction, catalysts may be optionally removed by filtration or centrifugation. Said catalysts may notably be recycled to the reactor.

Amines of interest can be purified by well-known methods of the technical field, such as distillation, crystallization, liquid extraction or extraction with a polymer to adsorb amines. Primary, secondary and/or tertiary amine may be isolated accordingly.

The examples provided here further describe and demonstrate embodiments of the present invention. The examples are given solely for the purpose of illustration and are not to be construed as limitation of the present invention.

EXPERIMENTAL PART

The supported Pd catalyst is prepared by incipient wetness impregnation of a high-surface-area ceria (Solvay HSA5, SBET 250 $m^2/g$) with aqueous solution of palladium (II) nitrate dihydrate. In a typical process, 0.15 g of palladium nitrate (~40 wt % Pd) is dissolved into 1.3 mL of deionized water, and the resulting solution was added into 2.94 g of $CeO_2$ slowly while keep stirring. After impregnation for 2 hours, the sample was dried at 120° C. overnight and then calcined in air at 400° C. for 2 hours.

The following amination reaction between 1-octanol and $NH_3$ was used to compare the performance of the Pd/CeO2 catalyst and other amination catalysts.

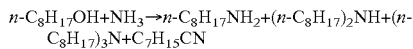

$n\text{-}C_8H_{17}OH+NH_3 \rightarrow n\text{-}C_8H_{17}NH_2+(n\text{-}C_8H_{17})_2NH+(n\text{-}C_8H_{17})_3N+C_7H_{15}CN$ The secondary amine is considered as the target product. The results are summarized in the following table.

TABLE 1

Amination of 1-octanol with $NH_3$ on various Pd-based catalysts

| Catalyst | Octanol conversion (%) | Selectivity (%) | | | |
|---|---|---|---|---|---|
| | | $C_8H_{17}NH_2$ | $(C_8H_{17})_2NH$ | $(C_8H_{17})_3N$ | $C_7H_{15}CN$ |
| Reduced Pd/CeO₂ (2 wt % Pd) | 48 | 14 | 51 | 18 | 17 |
| Pd/CeO₂ (2 wt % Pd) | 22 | 30 | 28 | 9 | 33 |
| Reduced Pd/C (5 wt % Pd) | 0 | — | — | — | — |
| Reduced Pd/Al₂O₃ (2 wt % Pd) | 0 | — | — | — | — |
| Reduced Pd/SiO₂ (2 wt % Pd) | 0 | — | — | — | — |
| Reduced Pd/TiO₂ (2 wt % Pd) | 0 | — | — | — | — |
| Reduced Pd/MgO (2 wt % Pd) | 0 | — | — | — | — | wt % is expressed with the total weight of catalyst.

Reaction conditions: 1.4 mmol 1-octanol, 3 mL tert-amyl alcohol, 8 bar $NH_3$ gas (~10 mmol), 70 mg catalyst, 180° C., 4 h.

"Reduced" means reduction in a flow of hydrogen at 300-500° C. The exact temperature was determined by temperature-programmed reduction.

It appears then that the catalyst of the present invention provided higher conversion and selectivity in the amination reaction in comparison with the other catalysts known in the prior art.

The invention claimed is:

1. A process to produce at least one amine, the process comprising at least reacting:
   1) a first reactant being an alkyl alcohol comprising one primary or secondary hydroxyl group; and
   2) a second reactant being ammonia and/or an ammonia source;
   in the presence of a catalyst comprising at least a palladium compound on a support comprising a cerium oxide.

2. The process according to claim 1 wherein the support of the catalyst comprises between 50-100% by weight of cerium oxide, based on the total weight of the support.

3. The process according to claim 1 wherein the cerium oxide provides a specific surface comprised between 50 and 300 $m^2/g$, measured after calcination at a temperature of 350° C. for 2 hours.

4. The process according to claim 1 wherein the palladium compound is chosen from the group consisting of: palladium metal, PdO, $PdO_2$, palladium nitrate, palladium chloride, palladium acetate, palladium acetylacetonate, and palladium hydroxide.

5. The process according to claim 1 wherein the catalyst is obtained by impregnation or co-precipitation.

6. The process according to claim 1 wherein the weight ratio of the catalyst to the second reactant is comprised between 0.05 and 2.

7. The process according to claim 1 wherein the first reactant comprises an alkyl chain comprising from 1 to 40 carbon atoms.

8. The process according to claim 1 wherein the first reactant is a compound of formula (I) $R^1$—OH or formula (II) $R^2$—C(OH)—$R^3$, wherein $R^1$, $R^2$, and $R^3$ are independently an alkyl group comprising from 1 to 40 carbon atoms.

9. The process according to claim 1 wherein the first reactant is a compound of formula (I) $R^1$—OH or formula (II) $R^2$—C(OH)—$R^3$, wherein $R^1$, $R^2$, and $R^3$ are independently an alkyl group comprising from 4 to 20 carbon atoms.

10. The process according to claim 1 wherein the first reactant is chosen from the group consisting of: 1-butanol, 1-hexanol, 1-octanol, 1-decanol, 1-dodecanol, 2-butanol, 2-hexanol, 3-hexanol, 2-octanol, 3-octanol and 4-octanol.

11. The process according to claim 1 wherein the second reactant is ammonia.

12. The process according to claim 1 wherein ammonia is gaseous ammonia, liquid ammonia, or an ammonia solution in a solvent.

13. The process according to claim 1 wherein the obtained amine is chosen from the group consisting of: octylamine, dioctylamine, trioctylamine, butylamine, dibutylamine, tributylamine, hexylamine, dihexylamine, trihexylamine, decylamine, didecylamine, tridecylamine, dodecylamine, didodecylamine, and tridodecylamine.

14. The process according to claim 1 wherein the reaction medium comprises at the start of the reaction, between 0.1 and 50 molar equivalent of the second reactant for 1 molar equivalent of the first reactant.

* * * * *